United States Patent [19]

Kawara et al.

[11] Patent Number: 5,020,085
[45] Date of Patent: May 28, 1991

[54] X-RAY IMAGE PROCESSING DEVICE

[75] Inventors: Toshiyuki Kawara, Moriguchi; Hiroshi Tsutsui, Yawata; Hiromasa Funakoshi, Hirakata; Yoshiyuki Yoshizumi, Suita, all of Japan

[73] Assignee: Matsushita Electric Industrial Co., Ltd., Osaka, Japan

[21] Appl. No.: 510,687

[22] Filed: Apr. 18, 1990

[30] Foreign Application Priority Data

Apr. 19, 1989 [JP] Japan .................. 64-99421

[51] Int. Cl.⁵ .................. H05G 1/64; G21K 3/00
[52] U.S. Cl. .................. 378/99; 378/146; 378/62; 378/156; 378/5
[58] Field of Search .................. 378/5, 19, 99, 146, 378/100, 111, 62, 156; 364/414

[56] References Cited

U.S. PATENT DOCUMENTS

| | | | |
|---|---|---|---|
| 4,686,695 | 8/1987 | Macovski | 378/146 |
| 4,692,937 | 9/1987 | Sashin et al. | 378/62 |
| 4,731,807 | 3/1988 | Plessis et al. | 378/156 |
| 4,761,739 | 8/1988 | Shimura | 364/414 |
| 4,853,947 | 8/1989 | Haaker et al. | 378/99 |
| 4,887,604 | 12/1989 | Shefer et al. | 378/144 |
| 4,926,454 | 5/1990 | Haendle et al. | 378/99 |
| 4,969,175 | 11/1990 | Nelson et al. | 378/146 |

OTHER PUBLICATIONS

Dual-Energy X-Ray Diagnostics, Phillips Technical Review, 42, No. 8/9, 274–285, Jun. 1986.

Primary Examiner—Carolyn E. Fields
Assistant Examiner—Kim-Kwok Chu
Attorney, Agent, or Firm—Wenderoth, Lind & Ponack

[57] ABSTRACT

An X-ray image processing device using dual energy projection radiography method, wherein the low energy image and the high energy image are subjected to a subtraction processing to output a first image such as bone X-ray image, and the first image and the low energy image are subjected to another subtraction to output a second image such as a soft tissue X-ray image without deterioration of the X-ray image.

4 Claims, 3 Drawing Sheets

X-RAY IMAGE PROCESSING DEVICE

BACKGROUND OF THE INVENTION

1. Field of the Invention

The present invention relates to an x-ray image processing device for diagnostic use and industrial use.

2. Description of the Prior Arts

An X-ray image or X-ray picture of an object can be obtained by the difference of the X ray amounts passed every part of the object or as the contrast of the X ray amounts of the every part of the object, wherein the difference of the X-ray amounts are caused by the difference of the thickness and/or difference of the composition of the object. For example, in human tissues. The composition of bone is mainly calcium, and since the X-ray absorption amount of the bone is greater than other tissue, there can be displayed an image having contrast between the bone and other tissue.

In order to obtain an X-ray image of only bone or only other soft tissue, there has been known an energy subtraction method or a dual energy projection radiography wherein two X-rays of different energy such as 80 KV (kilo volts) and 120 KV of the X-ray excitation voltage are independently radiated to the object and the respective X-ray amounts of the X-ray images of the different energies are subjected to logarithmic conversion and differentiation or subtraction between the logarithmically converted values.

A conventional energy subtraction method will be explained hereinafter with reference to FIG. 1. A low energy X-ray image 1 and a high energy X-ray image 2 are applied to subtraction processing units 3 and 4 respectively. The low energy X-ray image 1 is a logarithmic conversion signal of a X-ray image information taken by using a low energy X-ray obtained a X-ray tube excited by such as 80 KV and the high energy X-ray image 2 is a logarithmic conversion signal of a X-ray image information taken by using a high energy X-ray obtained by a X-ray tube excited by such as 120 KV. Both of the X-ray images 1 and 2 are subjected to the subtraction processing in the subtraction processing 3 and 4 so as to obtain the processed image 5 and the processed image 6. The equations used in the respective subtraction processing 3 and 4 are $$\text{image } 5 = k1 \times \text{image } 1 - k2 \times \text{image } 2 \qquad (1)$$

$$\text{image } 6 = k3 \times \text{image } 1 - k4 \times \text{image } 2 \qquad (2)$$

In general, the picture quality of the image obtained by using the above equations is much deteriorated.

Assuming that the noise components of the images 1 and 2 are N1 and N2, the noise components of the processed images 5 and 6 are shown by $$(\text{noise of image } 5)^2 = (K1 \times N1)^2 + (K2 \times N2)^2 \qquad (3)$$

$$(\text{noise of image } 6)^2 = (K3 \times N1)^2 + (K4 \times N2)^2 \qquad (4).$$

As shown by the equations (3) and (4), the noise component of the obtained image is the sum of the square values of the noise of the original images. Particularly, in case of taking out a picture component from the images of which contrast difference is small or in case of taking out a image component of which a space frequency is high, the picture quality is much deteriorated. In addition, since, in the high energy X-ray, the difference of the absorption due to the difference of the composition is small compared to the low energy X-ray, the X-ray image of the high energy X-ray has a low contrast difference, the signal to the noise ratio is bad and therefore, the signal to noise ratio is much deteriorated.

SUMMARY OF THE INVENTION

An essential object of the present invention is to provide an X-ray image processing device in which the deterioration of the picture quality is few.

In order to accomplish the object, according to the present invention there is povided an x-ray image processing device in which the low energy image and the high energy image are subjected to a subtraction to output a first image, and the first image and the low energy image are subjected to a subtraction to output a second image.

DETAILED DESCRIPTION OF THE PREFERRED EMBODIMENTS

Figure 1:
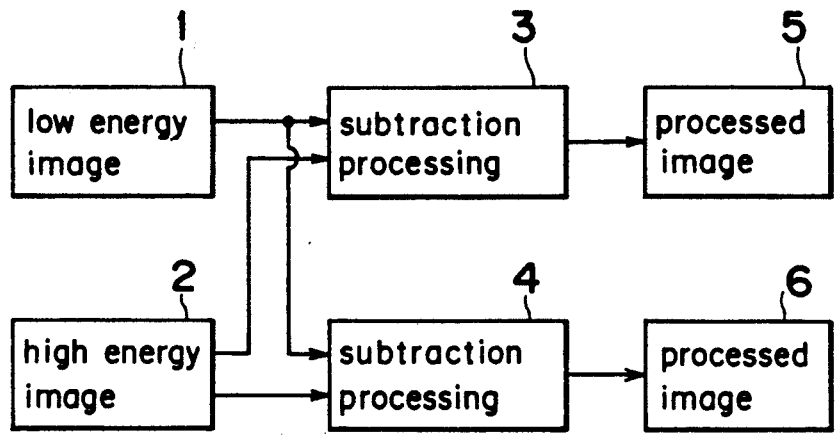
FIG. 1 is a block diagram showing an example of a conventional energy subtraction method.

Before the description proceeds, it is noted that like parts are designated by like reference numerals throughout the attached drawings.

Figure 2:
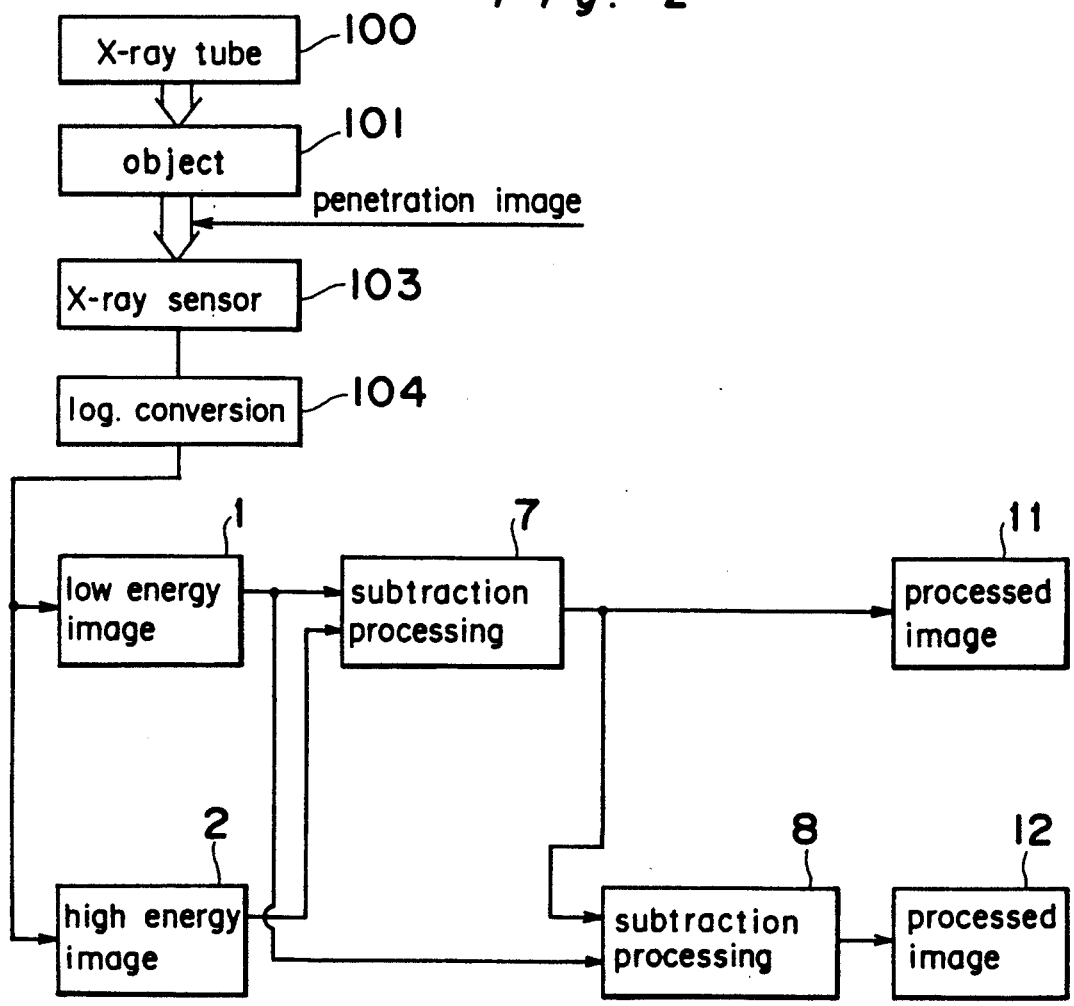
FIG. 2 is a block diagram of an embodiment of an X-ray image processing according to the present invention, FIG. 3 in a block diagram of a second embodiment of the X-ray image processing according to the present invention.

Referring to FIG. 2 showing the first embodiment of the X-ray image processing using the dual energy projection radiography method according to the present invention, one or more X-ray tube 100 irradiates X-ray of high energy or low energy to an object 101 such as a human body to be diagnosed by a radiography. The penetration X-ray image which has penetrated or passed the object 101 is sensed by a X-ray sensor 103 such as a line image sensor which outputs electrical image information representing the amount of the penetration X-ray image of every part of the object 101. The output image information of the X-ray sensor 103 is logarithmically converted in a logarithmic converter 104 which outputs the logarithmically converted information of the output of the X-ray sensor 103. As the arrangement of producing the logarithmically converted X-ray image information of the object as mentioned above, a known arrangement may be used and therefore description of the details thereof herein omitted.

In FIG. 2, 1 denotes a low energy X-ray image information which is supplied from the logarithmic converter 104 when the X-ray tube 101 is excited by a low energy such as 80 KV, 2 denotes a high energy X-ray image which is supplied from the logarithmic converter 104 when the X-ray is excited by a high energy such as 120 KV. There may be used various known arrangements to obtain the the low energy X-ray image and high energy X-ray image. 7 and 8 denote subtraction processing units, 11 denotes an image information after processing by the subtraction processing 7 and 12 denotes an image information after processing by the subtraction processing 8. The X-ray image processing shown in FIG. 2 will be explained hereinafter taking the X-ray penetration picture of a human body as an example.

The low energy X-ray image 1 and the high energy X-ray image 2 are subjected to the subtraction processing 7 using suitable factors for eliminating the human bone information and there can be obtained a processed image 11 or a soft tissue image 11 of the human body.

Subsequently, by performing the subtraction processing between the low energy X-ray image 1 and the soft tissue image 11 of the human body in the subtraction processing 8 using suitable factors, a processed image 12 or bone image 12 can be obtained. In general, in the image by the high energy X-ray, the contrast is low and a S/N ratio is also low. Therefore, according to the first embodiment shown in FIG. 2, there can be obtained the image with low noise compared to the conventional processed image obtained by the subtraction processing between the low energy X-ray image and the high energy X-ray image.

As mentioned above, According to the first embodiment, there is performed the first subtraction processing between the low energy X-ray image and the high energy X-ray image to obtain the subtraction processed image and further performed the second subtraction processing between the subtraction processed image and the low energy X-ray image, so that the aiming image component having a high frequency component can be obtained without increasing noise.

The above effect is explained using several equations.

Assuming $k1 = \mu_B(L)/\mu_B(H)$, $k2 = \mu_T(L)/\mu_T(H)$ wherein $\mu_B(L)$: the absorption factor of bone in the low energy $\mu_B(H)$: the absorption factor of bone in the high energy $\mu_T(L)$: the absorption factor of soft tissue in the low energy $\mu_T(H)$: the absorption factor of soft tissue in the high energy in general $k2 > k1 > 1$ Assuming noise in the low energy X-ray image $D_L$ is $N_L$ (which is relatively low), noise in the high energy X-ray image $D_H$ is $N_H$ (which is relatively high), noise in the soft tissue image image $D_T$ is $N_T$ noise in the bone image image $D_T$ is $N_B$, $$(N_T)^2 = (N_L)^2 + k_1^2 \times (N_H)^2 \quad 1$$

$$(N_B)^2 = (N_L)^2 + k_2^2 \times (N_H)^2 \quad 2$$

since $k_2 > k_1 > 1$ noise is contained in 2 more than 1
bone image $= D_L - k_3 \times D_T$ $$k_3 = \frac{k_2}{k_1 + k_2}$$

(noise in the bone image)$^2$ = $(N_L)^2 + k_3^2 \times (N_T)^2$

= $(1 + k_3^2)(N_L)^2 + k_1^2 k_3^2 (N_H)^2$ $(N_L)^2 << (N_H)^2$, since $k_1^2 k_3^2 < k_2^2$ noise is less than 2

$$\left[ \because k_2^2 - k_1^2 k_3^2 = k_2^2 - k_1^2 \left( \frac{k_2}{k_1 + k_2} \right)^2 = \right.$$

$$\left. \frac{k_2^2 \{(k_1 + k_2)^2 - k_1^2\}}{(k_1 + k_2)^2} = \frac{k_2^2 \times k_2 \times (2k_1 + k_2)}{(k_1 + k_2)^2} > 0 \right]$$

Figure 3:
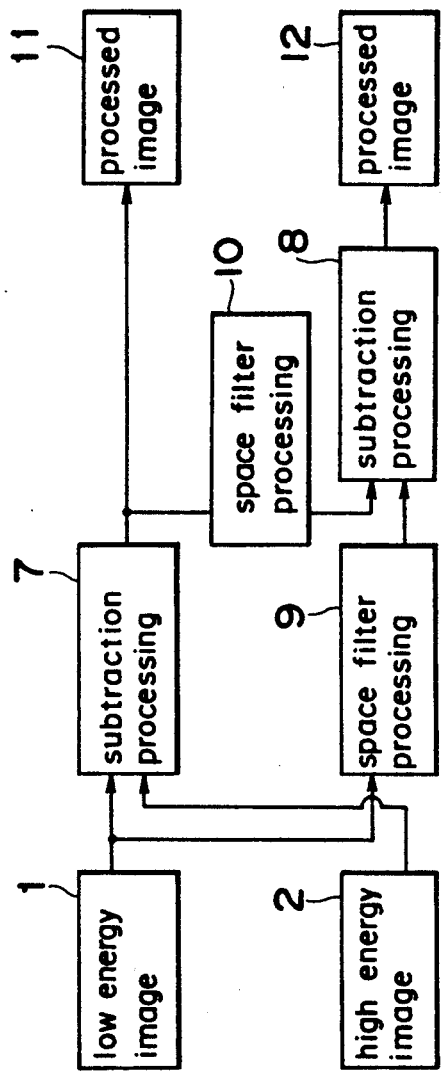

Referring to FIG. 3 showing the second embodiment of the present invention, 9 denotes a first space filter processing unit for enhancing high space frequency components of the X-ray image input to the space filtering processing unit 9, 10 denotes a second space filter processing unit to suppress the high space frequency components of the X-ray image applied thereto.

The X-ray image processing shown in FIG. 3 will be explained hereinafter taking the X-ray penetration image of a human body as an example.

In the subtraction processing 7, the low energy image 1 and the high energy image 2 are subjected to the subtraction processing using coefficients to eliminate the bone image, whereby there can be obtained the soft tissue image 11 of the human body as the processed image, which is subjected to the second space filter processing in the unit 10, wherein the high space frequency components for example the frequency components more than 2 line pair/mm are suppressed, whereby only the soft tissue image having only low space frequency components can be output. In general, since few high space frequency components are included in the soft tissue image of the human body, the information of the soft tissue is not lost in the second space filter processing in the unit 10 but the noise components of high frequency components can be eliminated.

On the other hand, the low energy X-ray image 1 is subjected to the first space filter processing in the unit 9 to enhance the high space frequency components for example, 2 line pairs/mm to 5 line pairs/mm. The high frequency components contained in the low energy image 1 are both of the high frequency components representing the bone image and noise components, and both of them are enhanced in the unit 9. However, since the noise components in the low energy X-ray image are not so high, the bone image is effectively enhanced, whereby there can be obtained an image having a high signal to noise ratio compared to the conventional method in which the high frequency components are enhanced after the subtraction processing is performed.

The result of the space filter processing in the unit 9 and the result of the space filter processing in the unit 10 are subjected to the subtraction processing 8. Namely, by subtracting the soft tissue image in which the high frequency components are suppressed and a suitable coefficient is multiplied, from the low energy X-ray image in which the high frequency components are enhanced, so that there is obtained the bone picture 12 as the processed image.

As mentioned above, according to the second embodiment, the image components containing the high frequency components can be obtained without deterioration of the picture quality by performing the subtraction processing between one processed image obtained by the subtraction processing between the low energy X-ray image and the high energy X-ray image with the high frequency components suppressed and another processed image of the low energy X-ray image with the high frequency components enhanced.

Figure 4:
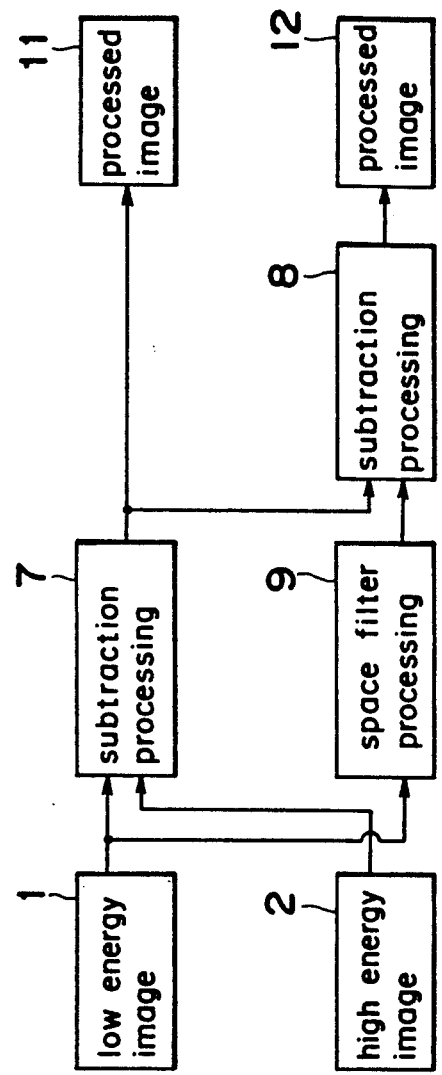
FIG. 4 is a block diagram of a third embodiment of the X-ray image processing according to the present invention.

Referring to FIG. 4 showing the third embodiment of the present invention, in which in the subtraction processing 7, the low energy X-ray image 1 and the high energy X-ray image 2 are subjected to the subtraction processing using factors to eliminate the bone image, whereby there can be obtained the soft tissue image 11 of the human body as the processed image. On the other hand, the low energy X-ray image 1 is subjected to the space filter processing in the unit 9 so that the high frequency components, for example the space frequencies of a range of 2 line pair/mm to 5 line pair/mm are enhanced. The result of the space filter processing 9 and the result of the subtraction processing 7 are subjected to the subtraction processing 8. Namely, by subtracting the soft tissue image in which the high frequency components are suppressed and a suitable factor is multiplied, from the low energy X-ray image in which the high frequency components are enhanced, so that there is obtained the bone image 12 as the processed image. Accordingly, in a case where the image of the object has the high frequency components other than the noise components in the result of the subtraction processing 7, the subtraction processing 8 can be performed very well. In addition, the processed image 12 can be obtained with the high frequency components enhanced, since the frequency enhancing process is performed using the low energy X-ray image 1 of which signal to noise ratio is highest, the enhancement of the noise component can be suppressed minimum.

As mentioned above, according to the third embodiment, in a case where such an object is X-ray photographed that the image components of the result of the subtraction processing between the low energy X-ray image and the high energy X-ray image contain the high frequency components other than the noise component, the image components can be obtained in a good condition by performing the subtraction processing between one processed image obtained by the subtraction processing between the low energy X-ray image and the high energy X-ray image and another processed image of the low energy X-ray image with the high frequency components enhanced.

Figure 5:
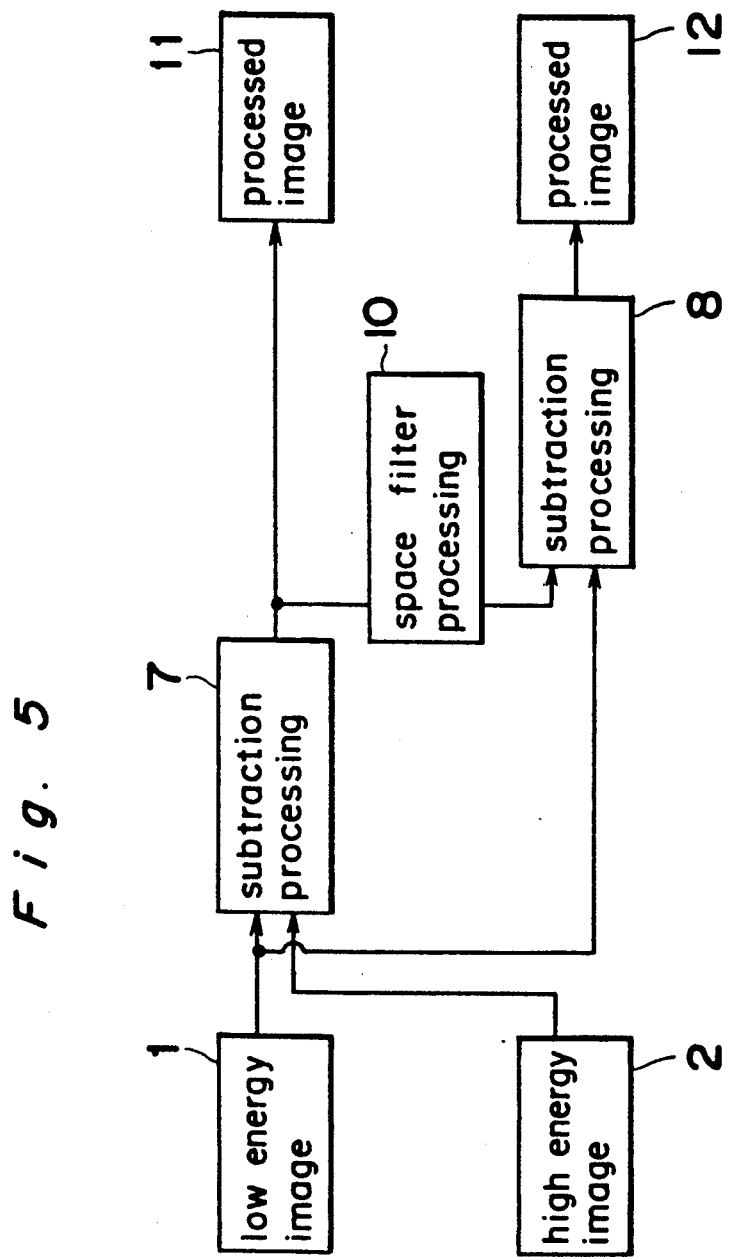
FIG. 5 is a block diagram of a fourth embodiment of the X-ray image processing according to the present invention.

Referring to FIG. 5 showing the fourth embodiment of the present invention, in which the space filter processing unit 10 is put between the subtraction processing 7 and the subtraction processing 8.

The X-ray picture processing shown in FIG. 5 will be explained hereinafter taking the X-ray penetration picture of a human body as an example.

In the subtraction processing 7, the low energy X-ray image 1 and the high energy X-ray image 2 are subjected to the subtraction processing 7 using factors to eliminate the bone image, whereby there can be obtained the soft tissue image 11 of the human body as the processed image On the other hand, the result of the subtraction processing 7 or the soft tissue image 11 is subjected to the space filter processing in the unit 10, in which the high space frequency components are suppressed so that the soft tissue image of the human body of the low space frequency components can be output. The result of the space filter processing 10 and the low energy X-ray image 1 are subjected to the subtraction processing 8. Namely, by subtracting the soft tissue image in which the high frequency components are suppressed and a suitable factor is multiplied, from the low energy X-ray image, so that there is obtained the bone image 12 as the processed image.

As mentioned above, according to the fourth embodiment, the low energy X-ray image and the high energy X-ray image are subjected to the energy subtraction processing and the high frequency components of its result is suppressed, subsequently, the high frequency component suppressed image and the low energy X-ray image are subjected to the further subtraction processing. In the above process, since the high frequency components are not enhanced, the noise component is not increased, whereby it is possible to take out the aiming image containing the high frequency components without deterioration of the picture quality even though the original image contains noise.

Although there are used in the second to third embodiments such high frequency filter processing of high frequency suppressing property and high frequency enhancing property, the present invention is not limited to the examples and there may be used various space filtering corresponding to the characteristics of the objects.

In order to obtain the high energy picture and the low energy picture, in place of taking the object two times by the X-ray tube excited by the different voltage such as 80 KV and 120 KV, the exciting voltage of the X-ray tube may be unchanged but a metal plate may be put between the X-ray tube and the X-ray sensor when the high energy picture is taken. Moreover, it may be possible to take the different energy pictures through one time picture taking using the X-ray sensor having a function of energy discrimination.

What is claimed is

1. An x-ray image processing device comprising;
   means for obtaining low energy image information which is logarithmic conversion image information of a penetration image of an object radiated by low energy X-ray,
   means for obtaining high energy image information which is logarithmic conversion image information of a penetration image of an object radiated by high energy X-ray,
   means for subtracting the low energy image information and the high energy image information to output a first image, and
   means for subtracting the first image and the low energy image information to output a second image.

2. An x-ray image processing device comprising;
   means for obtaining low energy image information which is logarithmic conversion image information of a penetration image of an object radiated by low energy X-ray,
   means for obtaining high energy image information which is logarithmic conversion image information of a penetration image of an object radiated by high energy X-ray,
   means for subtracting the low energy image information and the high energy image information to output a first image,
   means for suppressing high frequency component of the first image to output a high frequency suppressed image,
   means for enhancing high frequency component of the low energy image information to output a high frequency enhanced image, and means for subtracting between the high frequency suppressed image and the high frequency enhanced image to output a second image.

3. The X-ray image processing device according to claim 1, wherein said device further comprises;
means for suppressing high frequency component of the first image to output a high frequency suppressed image, and
means for subtracting between the high frequency suppressed image and the low energy image information to output the second image.

4. The X-ray image processing device according to claim 1, wherein said device further comprises;
means for enhancing high frequency component of the low energy image information to output a high frequency enhanced image, and
means for subtracting between the high frequency enhanced image and the first image to output the second image.

* * * * *